(12) United States Patent
Yanuma et al.

(10) Patent No.: US 7,648,525 B2
(45) Date of Patent: Jan. 19, 2010

(54) STENT DELIVERY SYSTEM AND INDWELLING METHOD FOR STENT

(75) Inventors: Yutaka Yanuma, Kunitachi (JP); Junichi Muramatsu, Akiruno (JP)

(73) Assignee: Olympus Corporation, Tokyo (JP)

( * ) Notice: Subject to any disclaimer, the term of this patent is extended or adjusted under 35 U.S.C. 154(b) by 504 days.

(21) Appl. No.: 10/718,188

(22) Filed: Nov. 20, 2003

(65) Prior Publication Data

US 2005/0090889 A1 Apr. 28, 2005

(30) Foreign Application Priority Data

Nov. 20, 2002 (JP) ............................. 2002-336908
Nov. 13, 2003 (JP) ............................. 2003-383230

(51) Int. Cl.
*A61F 2/06* (2006.01)
(52) U.S. Cl. .................................................. 623/1.11
(58) Field of Classification Search ................. 623/1.11, 623/1.12
See application file for complete search history.

(56) References Cited

U.S. PATENT DOCUMENTS

| | | | | |
|---|---|---|---|---|
| 4,653,477 A | * | 3/1987 | Akui et al. .................. 600/154 |
| 5,438,735 A | * | 8/1995 | Gayhart, Jr. ................... 24/335 |
| 5,733,267 A | * | 3/1998 | Del Toro ..................... 623/1.11 |
| 6,033,413 A | * | 3/2000 | Mikus et al. ................. 606/108 |
| 6,302,893 B1 | | 10/2001 | Limon et al. |
| 6,350,278 B1 | * | 2/2002 | Lenker et al. .............. 623/1.12 |
| 6,514,261 B1 | * | 2/2003 | Randall et al. .............. 606/108 |
| 2003/0083730 A1 | * | 5/2003 | Stinson ...................... 623/1.11 |
| 2006/0162731 A1 | * | 7/2006 | Wondka et al. .......... 128/207.14 |

FOREIGN PATENT DOCUMENTS

JP  2-39445  10/1990

* cited by examiner

*Primary Examiner*—Todd E Manahan
*Assistant Examiner*—Eric Blatt
(74) *Attorney, Agent, or Firm*—Scully, Scott, Murphy & Presser, P.C.

(57) ABSTRACT

There is disclosed a stent delivery system includes a first cylindrical member capable of being inserted into a forceps channel of an endoscope and including a through hole having a central axis; a second cylindrical member inserted into the through hole of the first cylindrical member and capable of advancing/retreating with respect to the first cylindrical member, the second cylindrical member including a holding mechanism which holds a relative position of the second cylindrical member with respect to the forceps channel of the endoscope, and a stent which is attached between the first and second cylindrical members in a state where a diameter of the stent is reduced by the first cylindrical member and which expands when the first cylindrical member is removed.

21 Claims, 9 Drawing Sheets

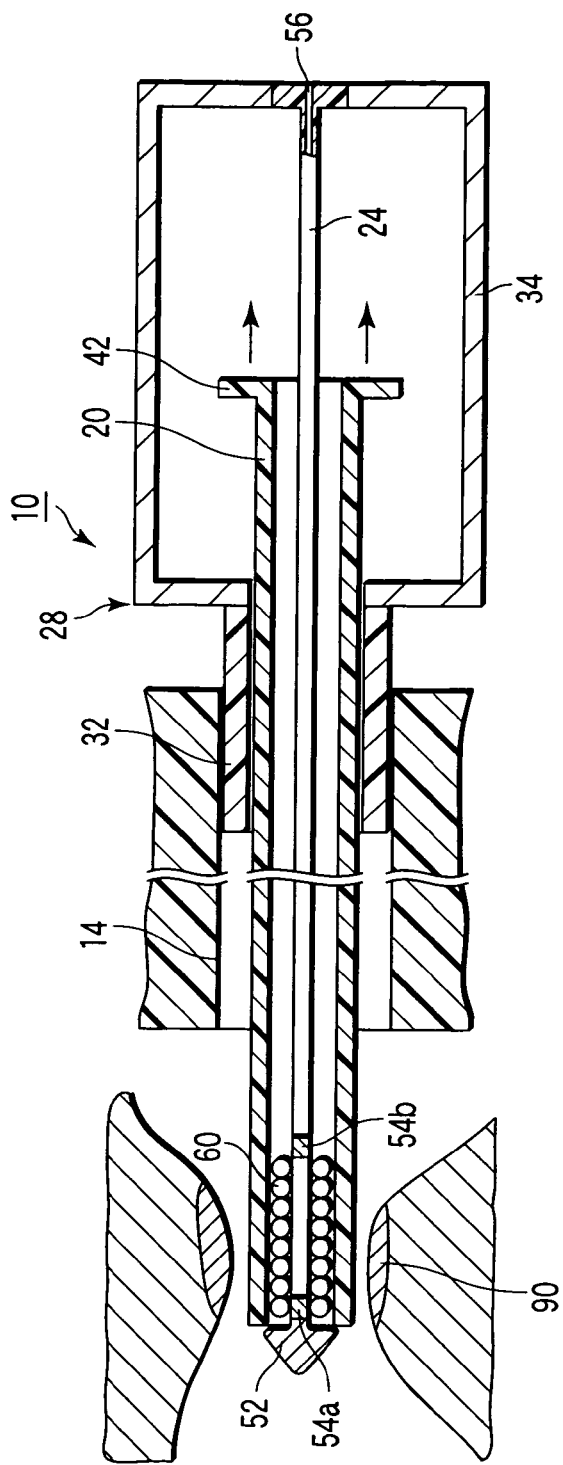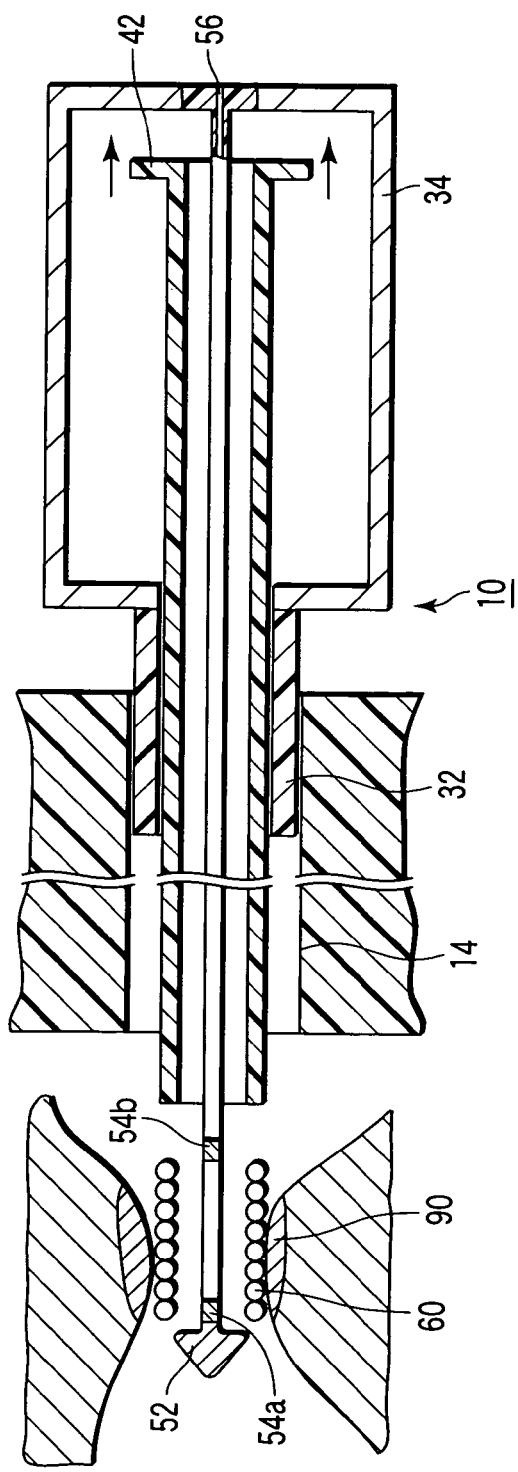

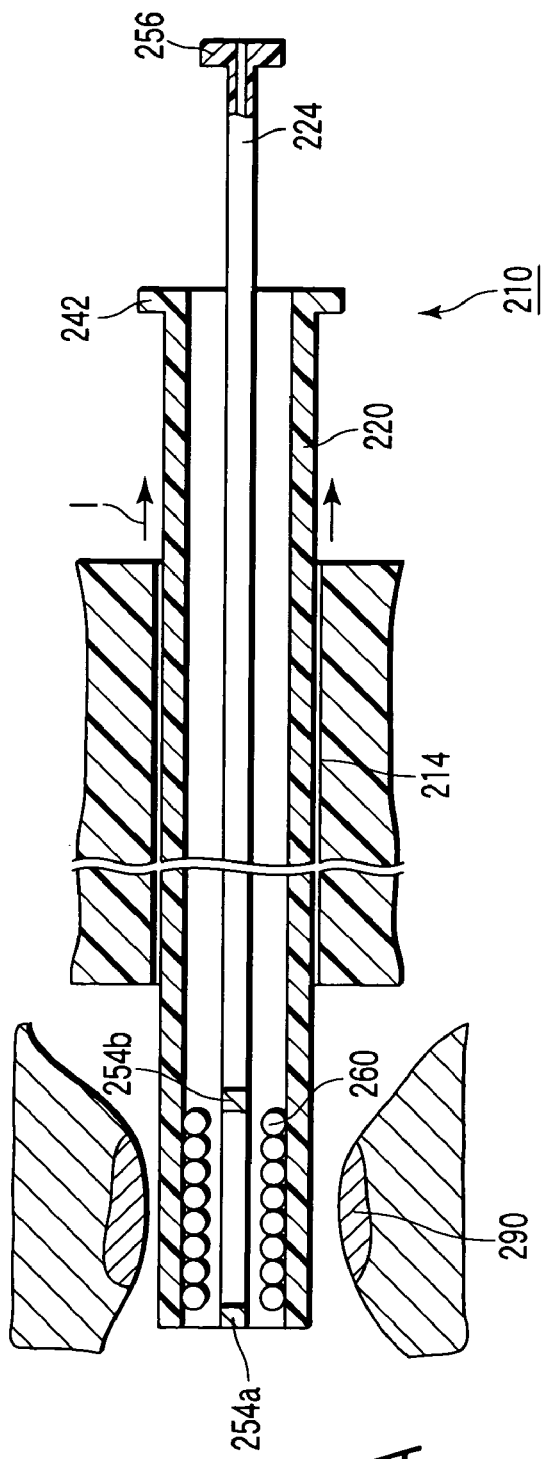
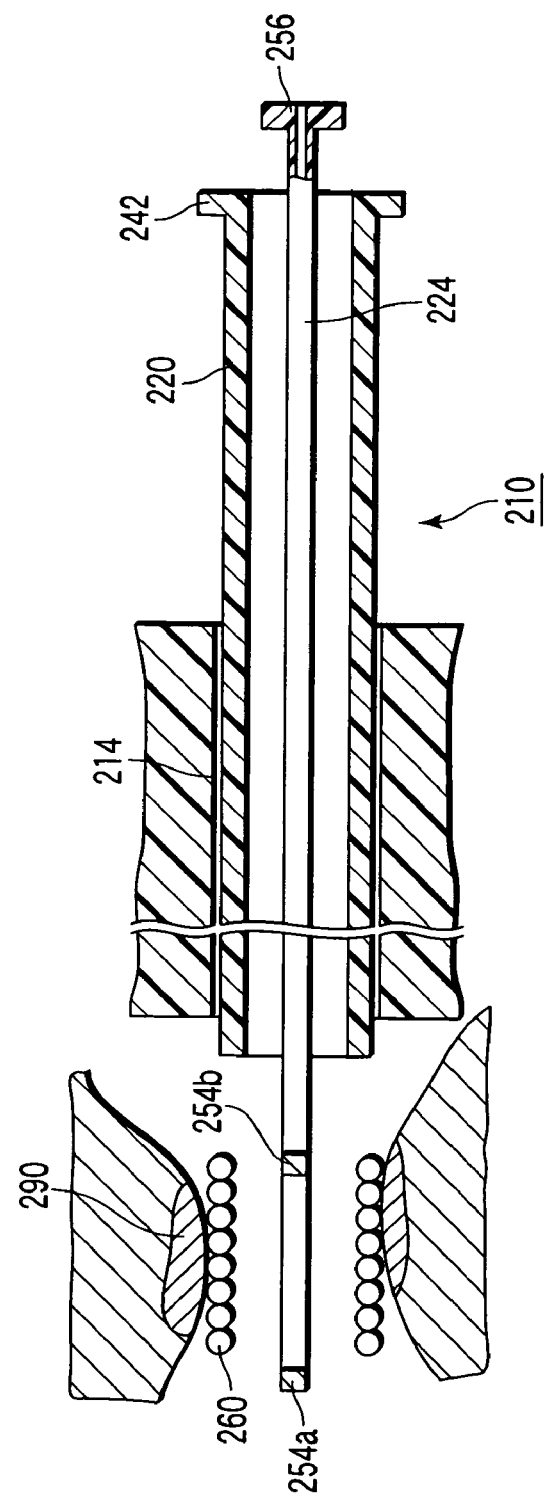
FIG. 11A PRIOR ART
FIG. 11B PRIOR ART

US 7,648,525 B2

STENT DELIVERY SYSTEM AND INDWELLING METHOD FOR STENT

CROSS-REFERENCE TO RELATED APPLICATIONS

This application is based upon and claims the benefit of priority from the prior Japanese Patent Applications No. 2002-336908, filed Nov. 20, 2002, and No. 2003-383230, filed Nov. 13, 2003, the entire contents of which are incorporated herein by reference.

BACKGROUND OF THE INVENTION

1. Field of the Invention

The present invention relates to a stent delivery system for use in indwelling a self-expansion type stent in a body cavity, and an indwelling method for a stent.

2. Description of the Related Art

There are known various techniques concerning a stent delivery system for indwelling a self-expansion type stent in a body cavity, as disclosed, for example, in U.S. Pat. No. 6,302,893.

FIGS. 10 to 11B show a conventional type of delivery system 210 in which a self-expansion type stent 260 is indwelled in the body cavity as one example of the stent delivery system. An outer cylinder 220 which contacts an inner wall of a forceps channel 214 of an endoscope 280 is disposed in the delivery system 210 as shown in FIG. 10. An inner cylinder 224, inserted so as to be capable of advancing and retreating, is disposed in the outer cylinder 220.

As shown in FIG. 10, in the delivery system 210, a doctor α who operates the endoscope 280, and a doctor β who operates the delivery system 210 move the outer cylinder 220 in a pull-out direction (arrow I direction) with respect to the forceps channel 214 (see FIG. 11A). The doctor α holds the inner cylinder 224 and prevents to move the inner cylinder 224. Then, the stent 260 attached to a tip end of the inner cylinder 224 is indwelled in a target position 290 in a bile duct confirmed using X-ray chips 254a, 254b (see FIG. 11B).

BRIEF SUMMARY OF THE INVENTION

According to one aspect of the present invention, there is provided a stent delivery system comprising: a first cylindrical member capable of being inserted into a forceps channel of an endoscope and including a through hole having a central axis; a second cylindrical member inserted into the through hole of the first cylindrical member and capable of advancing/retreating with respect to the first cylindrical member; and a stent which is attached between the second cylindrical member and the first cylindrical member in a state where a diameter of the stent is reduced by the first cylindrical member and which expands when the first cylindrical member is removed. The second cylindrical member includes a holding mechanism which holds a relative position of the second cylindrical member with respect to the forceps channel of the endoscope.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic partial sectional view of a stent delivery system in a state in which a stent is attached to a stent delivery system according to a first embodiment;

FIG. 1B is a schematic partial sectional view of the stent delivery system showing a state in which the stent of the stent delivery system according to the first embodiment is released from a regulated state;

FIG. 11A is a schematic partial sectional view of the stent delivery system in a state in which the stent is attached to the stent delivery system according to a prior art; and FIG. 11B is a schematic partial sectional view of the stent delivery system showing a state in which the stent of the stent delivery system according to the prior art is released from the regulated state.

DETAILED DESCRIPTION OF THE INVENTION

Embodiments of the present invention will hereinafter be described with reference to the drawings.

First, a first embodiment will be described with reference to FIGS. 1A to 7.

As schematically shown in FIGS. 1A and 1B, a stent delivery system 10 according to this embodiment includes three layers of cylindrical members on a concentric axis so that first to third layers are formed.

Figure 7:
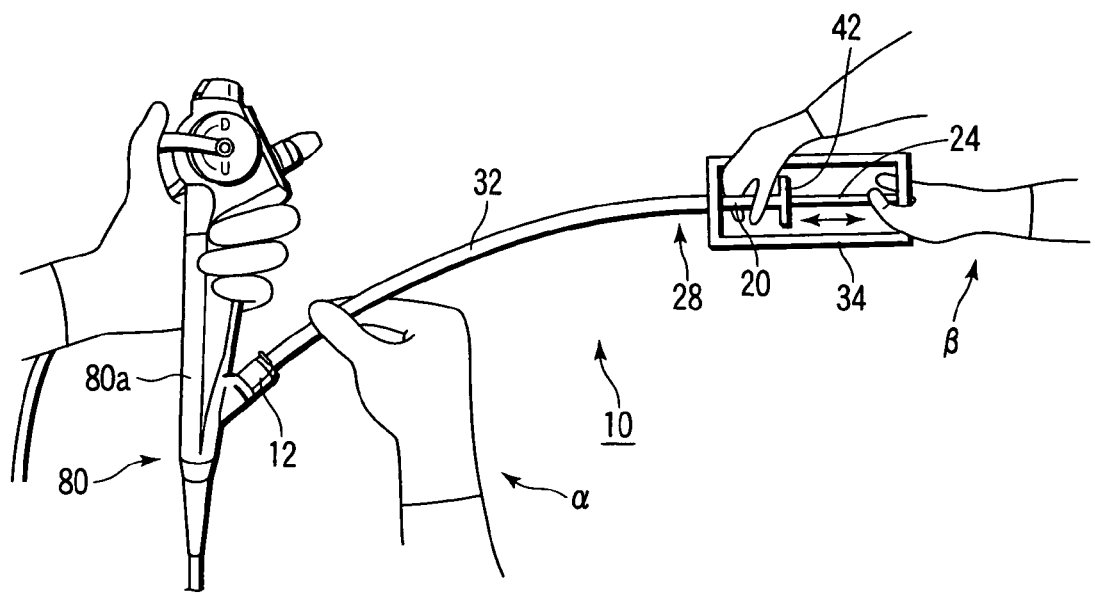
FIG. 7 is a schematic diagram showing a state in which the stent delivery system according to the first embodiment is attached to the channel of the endoscope.
Figure 10:
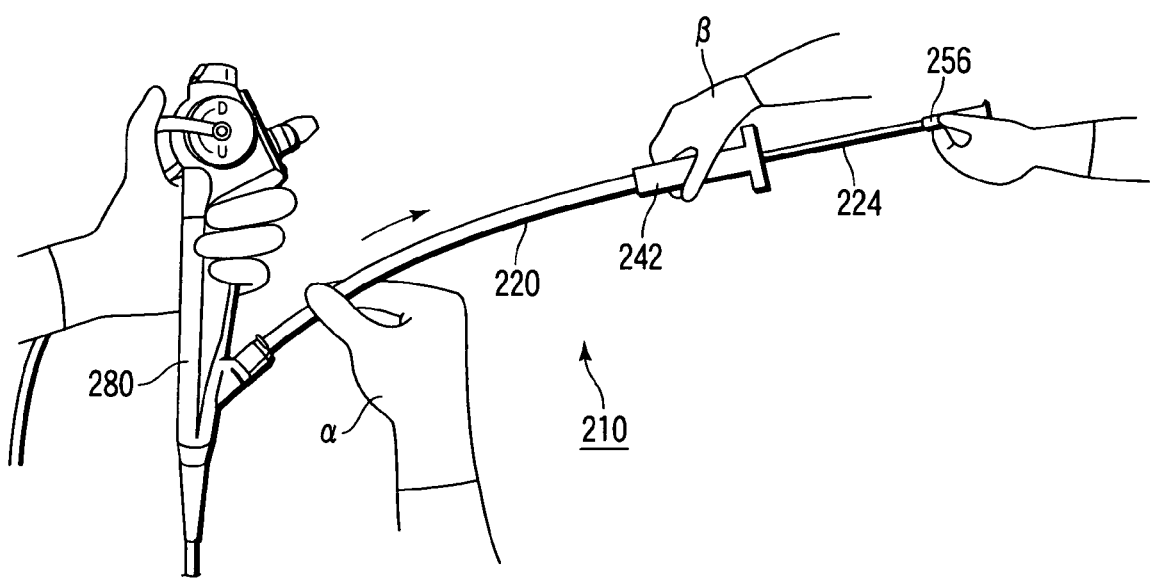
FIG. 10 is a schematic diagram showing a state in which the stent delivery system according to a related art is attached to the channel of the endoscope.

As a first cylindrical member, a flexible outer cylinder 20 is disposed which can be inserted through a forceps channel 14 of an endoscope from an opening 12a (see FIG. 2) of a forceps cap 12 disposed in an endoscope 80 (see FIG. 7). As a second cylindrical member, a flexible inner cylinder 24 is disposed which is concentrically inserted into the outer cylinder 20 and which can advance/retreat with respect to the outer cylinder 20. An outermost cylinder 28 is disposed as a third cylindrical member further on an outer periphery of the outer cylinder 20 with respect to the second cylindrical member, that is, the inner cylinder 24. The outermost cylinder can directly slide on the outer cylinder 20, and a part of the cylinder is inserted in the forceps channel 14 from the opening 12a of the forceps cap 12.

The outermost cylinder 28 includes a flexible cylindrical portion 32 capable of being partially inserted in the forceps channel 14 via the opening 12a of the forceps cap 12, and a connection member 34 disposed on a base end of the cylindrical portion 32 and connected to a base end 56 of the inner cylinder 24 described later. The connection member 34 is formed, for example, in a schematically rectangular annular shape.

An outer peripheral surface of the cylindrical portion 32 contacts the inner walls of the forceps cap 12 and forceps channel 14, and accordingly the cylindrical portion 32 is engaged with the forceps cap 12 and forceps channel 14 by the friction. Therefore, the cylindrical portion 32 is schematically fixed with respect to the forceps cap 12 and forceps channel 14. Therefore, the cylindrical portion (fixing portion) 32 of the outermost cylinder 28 functions as a fixing mechanism (holding mechanism) for fixing the outermost cylinder 28 with respect to the forceps cap 12 and forceps channel 14.

An outer cylinder grasp portion (flange portion) 42 projected toward the outside in a diametric direction is disposed in the base end of the outer cylinder 20. The tip end and vicinity of the outer cylinder 20 are preferably coated with a hydrophilic lubricating coat so as to improve inserting/passing properties into the forceps channel 14 of the endoscope 80 or the body cavity.

A flexible guide wire (not shown) can be inserted in the through hole in the inner cylinder 24. A substantially conical (truncated conical) tip-end chip 52 whose tip end is opened so as to pass the guide wire is disposed on the tip end of the inner cylinder 24. The outer peripheral surface of the tip-end chip 52 is preferably coated with the hydrophilic lubricating coat so as to improve the inserting/passing properties into the forceps channel 14 of the endoscope 80 and the body cavity. X-ray chips 54a, 54b are disposed on the rear end of the tip-end chip 52, that is, in the vicinity of the tip end of the inner cylinder 24 and in a position distant from the vicinity of the tip end on a base-end side by a predetermined distance. These X-ray chips 54a, 54b are disposed so as to confirm an inserted position of the tip end of the inner cylinder 24 or a self-expansion type cylindrical stent 60 (see FIG. 3) by use of X-rays. For example, the stent 60 with the reduced diameter is disposed on the X-ray chips 54a, 54b between the inner cylinder 24 and the outer cylinder 20. Static and dynamic frictions between the inner surface of the stent 60 and the outer peripheral surface of the inner cylinder 24 are sufficiently larger than the dynamic friction between the outer surface of the stent 60 and the outer cylinder 20.

The base end 56 of the inner cylinder 24 is formed substantially in a T shape, and is connected to the connection member 34 of the outermost cylinder 28. The inner cylinder 24 includes the outermost cylinder 28 connected to the base end 56, and the inner cylinder 24 and outermost cylinder 28 operate together. Then, when the inner cylinder 24 is inserted in the forceps cap 12 or the forceps channel 14, the inner cylinder is substantially fixed by the cylindrical portion 32 of the outermost cylinder 28. The base end 56 is also opened so that the guide wire is inserted into the end.

Figure 4:
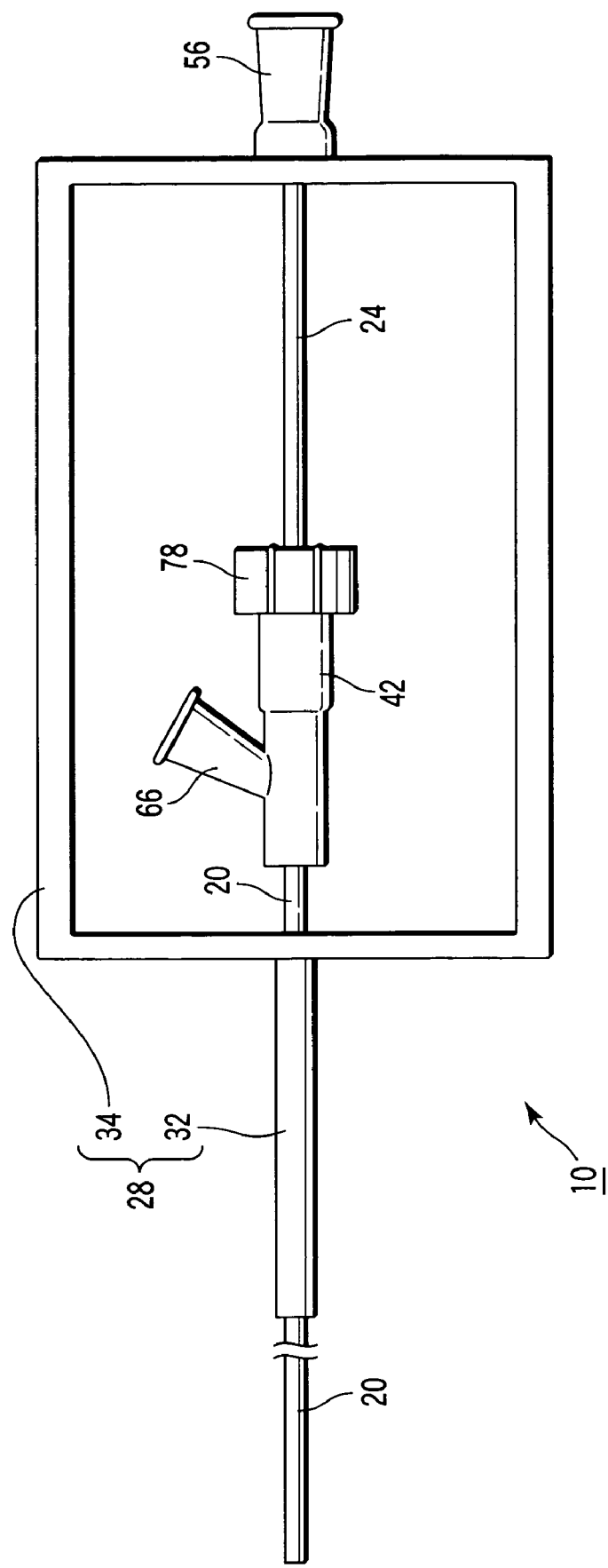
FIG. 4 is a schematic diagram showing a constitution of the stent delivery system according to the first embodiment.
Figure 5:
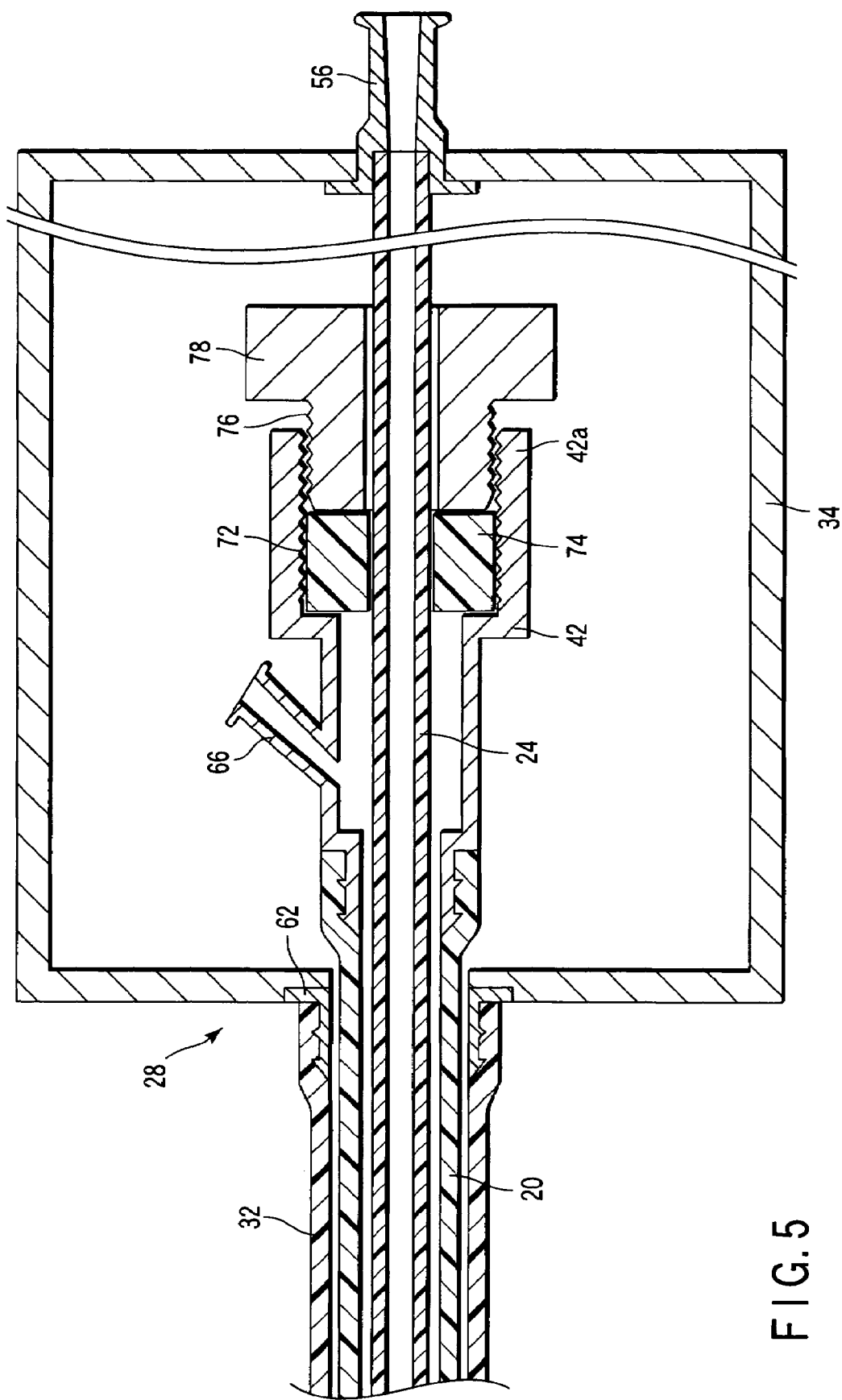
FIG. 5 is a schematic sectional view showing the constitution of the stent delivery system according to the first embodiment.
Figure 6:
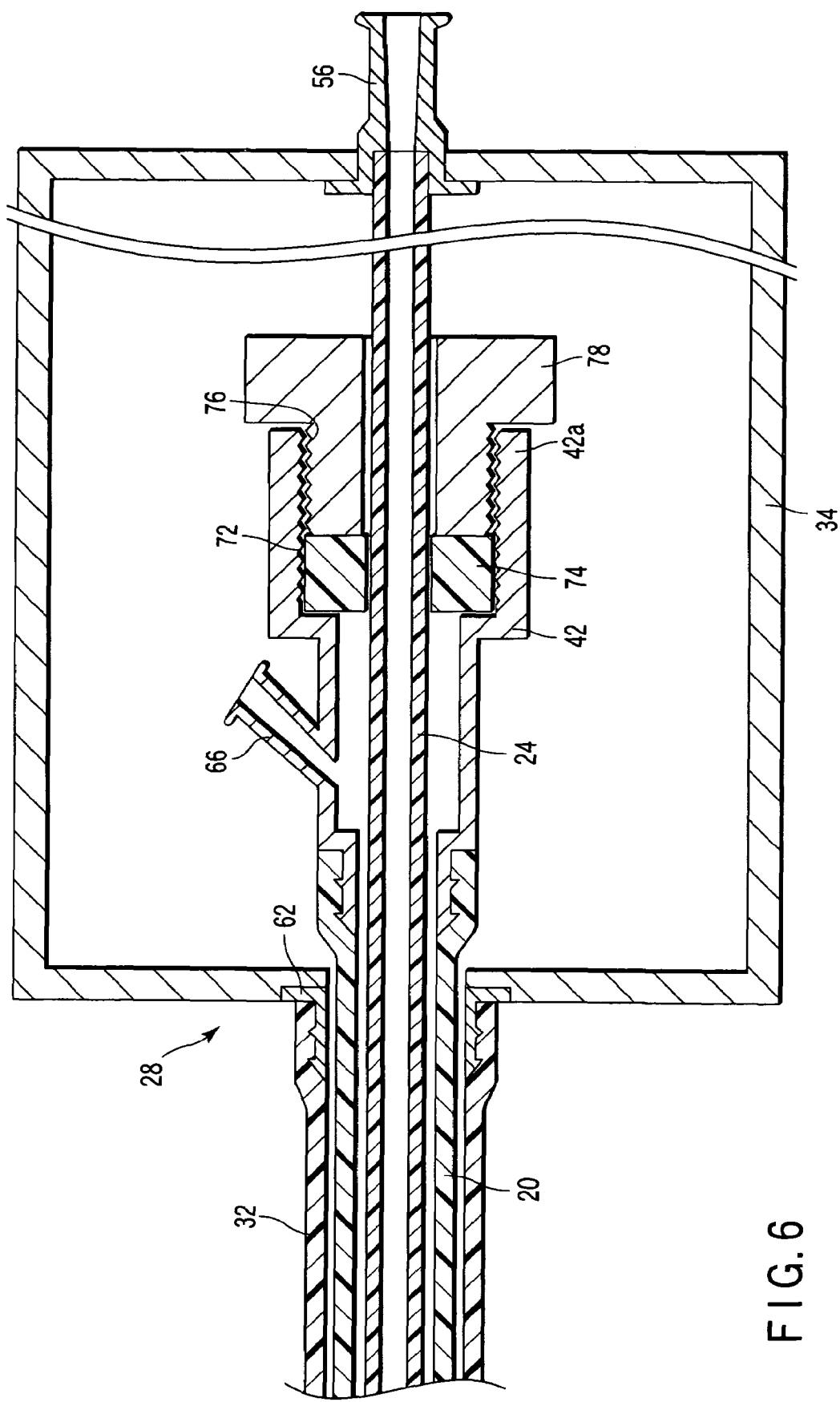
FIG. 6 is a schematic sectional view showing the constitution of the stent delivery system according to the first embodiment.

Concretely, the stent delivery system 10 is formed as shown in FIGS. 4 to 6 on a hand side. As shown in FIG. 5, a cylindrical engagement member 62 extending forwards along the axial direction of the inner cylinder 24 and including a protrusion for engagement on the tip end is disposed on the tip end of the connection member 34. Since the protrusion for engagement of the engagement member 62 engages with the inner peripheral surface of the base end of the cylindrical portion 32, the cylindrical portion 32 is connected to the connection member 34. A port 56 opened to pass the guide wire is disposed on the same axis as that of the inner cylinder 24 in the base end of the inner cylinder 24. The rear end of the connection member 34 is attached to the port 56. The inner cylinder 24 is connected to the outermost cylinder 28 in this manner.

The connector (outer cylinder grasp portion) 42 is attached to the base end of the outer cylinder 20. The tip end of the connector 42 has substantially the same inner and outer diameters as those of the outer cylinder 20, and the base end thereof includes an enlarged diameter portion 42a having a diameter larger than that on the tip-end side. In the tip end of the connector 42, a water feed port 66 is formed obliquely upwards on the hand side in FIGS. 4 and 5. A female screw portion 72 is formed on the inner peripheral surface of the enlarged diameter portion 42a. A bond ring 74 formed of soft materials such as a silicone rubber material is disposed on the tip end inside the enlarged diameter portion 42a. A rotary ring 78 on which a male screw portion 76 is formed is disposed on the base end of the bond ring 74.

Therefore, the bond ring 74 is reduced and enlarged in the axial direction of the inner cylinder 24 by a meshing degree between the female screw portion 72 of the enlarged diameter portion 42a and the male screw portion 76 of the rotary ring 78, and is also deformed so as to be enlarged and reduced in a diametric direction crossing at right angles to the axial direction. Since the bond ring 74 is enlarged and reduced in the diametric direction crossing at right angles to the axial direction of the rotary ring 78, the bond ring is detachably attached to the outer periphery of the inner cylinder 24, and is detachably attached to the inner periphery of the outer cylinder 20. Then, when the rotary ring 78 is tightened or released with respect to the connector 42, the outer cylinder 20 and inner cylinder 24, and the outer cylinder 20 and outermost cylinder 28 can be switched between a fixed state and a released state.

The stent delivery system 10 is formed in this manner.

Next, the function of the stent delivery system 10 of the present embodiment will be described. As shown in FIG. 7, it is assumed that a doctor α grasps and operates mainly the endoscope 80, and a doctor β grasps and operates mainly the connection member 34 of the stent delivery system 10.

The doctor α or β charges the self-expansion type stent 60 with the reduced diameter in a predetermined position between the inner peripheral surface of the outer cylinder 20 of the stent delivery system 10 and the outer peripheral surface of the inner cylinder 24, here on the X-ray chips 54a, 54b disposed on the inner cylinder 24 beforehand (see FIG. 1A). The doctor α or β rotates the rotary ring 78 shown in FIG. 5 in a tightening direction. Then, the bond ring 74 in a free state is elastically deformed in the axial direction so that the ring is crushed in the enlarged diameter portion 42a of the connector 42, and the diameter of the ring is enlarged in the diametric direction. The bond ring 74 is allowed to abut on the outer periphery of the inner cylinder 24 and the inner cylinder 24 and outer cylinder 20 are brought into a fixed state in this manner. That is, the relative positions of the inner cylinder 24 and outermost cylinder 28 with respect to the outer cylinder 20 are brought in the fixed state (immobile state) (see FIG. 6).

The doctor α passes the guide wire through the forceps channel 14 of the endoscope 80 to introduce the tip end of the guide wire into a bile duct in a trans-papillary manner. The doctor α is careful not to move the tip end of the guide wire while holding the guide wire. The doctor β passes the base end of the guide wire through the inner cylinder 24 from the tip-end chip 52 to pass the guide wire through the stent delivery system 10.

The doctor α inserts the stent delivery system 10 into the forceps channel 14 from the forceps cap 12 of the endoscope 80, and introduces the tip end of the stent delivery system 10 into the bile duct in the trans-papillary manner along the guide wire inserted in the inner cylinder 24. Therefore, the tip end and vicinity of the outer cylinder 20 and inner cylinder 24 are inserted into the bile duct in the trans-papillary manner.

The doctor α confirms the positions of the X-ray chips 54a, 54b disposed on the inner cylinder 24 under X-ray illumination while advancing/retreating the outermost cylinder 28 of the stent delivery system 10 with respect to the forceps cap 12 and forceps channel 14 to determine a position where the stent 60 is indwelled (tumor portion (stenosed portion) 90). Therefore, an insertion length of the stent delivery system 10 into the forceps channel 14 is determined. The cylindrical portion 32 of the outermost cylinder 28 of the stent delivery system 10 is substantially fixed by the friction between the forceps cap 12 and the forceps channel 14.

The doctor α who operates the endoscope 80 in this state operates the endoscope 80 so as to prevent the position of the stent 60 from deviating from the tumor portion 90, and holds the endoscope 80. The doctor α holds the stent delivery system 10, for example, in the vicinity of the forceps cap 12 in such a manner that the stent delivery system 10 is immobile with respect to the forceps cap 12 and forceps channel 14.

The doctor β who operates the connection member 34 of the stent delivery system 10 rotates the rotary ring 78 in the state shown in FIG. 6 in a loosening direction, while the connection member 34 is held. The fixed state between the inner cylinder 24 and the outer cylinder 20 is released. The fixed state between the outer cylinder 20 and the outermost cylinder 28 is released (see FIG. 5).

The doctor β slowly pulls in the connector 42 on the base end of the outer cylinder 20 on the hand side in the state in which the connection member 34 is held. That is, the rotary ring 78 is moved in the vicinity of the port 56 of the inner cylinder 24. Since the outermost cylinder 28 is substantially in the fixed state with respect to the forceps cap 12 and forceps channel 14, the inner cylinder 24 operating together with the outermost cylinder 28 is held in the indwelled position. Since the static and dynamic frictions between the stent 60 and the outer peripheral surface of the inner cylinder 24 are sufficiently larger than the dynamic friction between the stent and the inner peripheral surface of the outer cylinder 20, the stent is disposed and held on the tip end of the inner cylinder 24. Therefore, the outer cylinder 20 is relatively pulled back toward the inner cylinder 24 on the hand side. Therefore, the outer cylinder 20 is relatively drawn back with respect to the forceps cap 12 or the forceps channel 14 on the hand side. Then, in the tip end of the stent delivery system 10, the outer cylinder 20 is gradually detached from the outer periphery of the stent 60 and loses a regulating force for reducing the diameter of the stent 60, and the stent 60 expands on the tip-end side.

When the connector 42 is further pulled in on the hand side, the outer cylinder 20 moves rearwards (hand side) with respect to the inner cylinder 24. The stent 60 is exposed with respect to the body cavity, expands toward the rear end, and is released from the outer cylinder 20. The stent 60 is indwelled in the desired position (tumor portion 90) in the body cavity in this manner.

The doctor α moves the stent delivery system 10 in a pull-out direction from a state in which the stent delivery system 10 is disposed in the forceps cap 12 and forceps channel 14 while, for example, the endoscope 80 remains to be held. In this case, the stent delivery system 10 is pulled out against a fixing force by which the system is fixed with respect to the forceps cap 12 or the forceps channel 14 of the outermost cylinder 28. Therefore, the tip-end chip 52 disposed on the tip end of the inner cylinder 24 is pulled out through the inner hole of the stent 60 on the hand side from the stent 60. The stent delivery system 10 is further pulled back on the hand side to pull the tip end of the stent delivery system 10 from the bile duct. At this time, treatment may further be carried out in a state in which the tip end of the guide wire is held in the bile duct, and the guide wire may also be pulled out together with the stent delivery system 10.

As described above, the following effect is obtained by the stent delivery system 10 of the present embodiment.

The inner cylinder 24 is connected to the outermost cylinder 28 substantially fixed to the forceps cap 12 and forceps channel 14 of the endoscope 80, and the outer cylinder 20 is disposed between the outermost cylinder 28 and the inner cylinder 24 so as to be capable of advancing/retreating. When the outer cylinder 20 is operated in this state, only the outer cylinder 20 relatively advances/retreats with respect to the forceps cap 12 and forceps channel 14, and the position of the inner cylinder 24 is held. Therefore, the positional deviation of the inner cylinder 24 in which the stent 60 is charged is prevented, whereas the stent 60 can be indwelled in the desired position.

Therefore, when the stent 60 is released, both the doctors α and β do not have to adjust the timings or to simultaneously carry out the operation, and a troublesome operation can be eliminated. Then, the operability of the stent delivery system can be enhanced.

Therefore, the doctor α can concentrate mainly on the operation of the endoscope 80, and the doctor β can concentrate on the operation of the stent delivery system 10, respectively. While the positional deviation of the stent 60 is prevented, the stent 60 can easily be indwelled in the desired position.

Since the outermost cylinder 28 directly slides on the outer cylinder 20, an extra space is removed, and the diameter of the stent delivery system 10 can be prevented from being enlarged.

Figure 2:
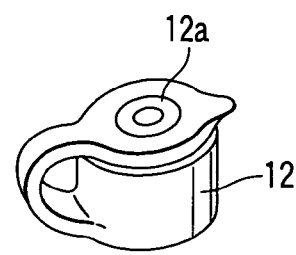
FIG. 2 is a schematic diagram showing a forceps cap to be attached to a base end of a forceps channel of an endoscope for attachment of the stent delivery system according to the first embodiment.
Figure 3:
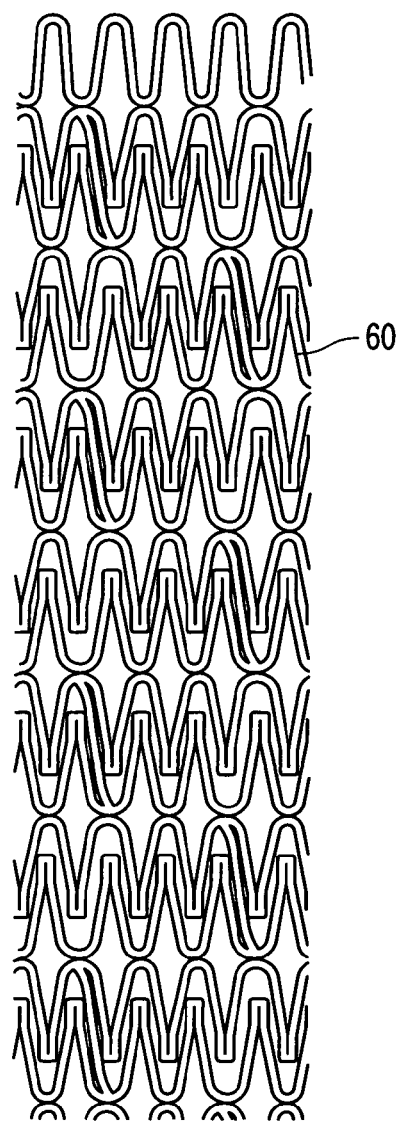
FIG. 3 is a schematic diagram showing a part of the surface of a self-expansion type stent disposed in the stent delivery system according to the first embodiment.

It is to be noted that the present embodiment has been described by the use of the stent 60 having the surface shown in FIG. 3, but the stent is not limited to this shape as long as the stent is of the self-expansion type. For example, the stent may also be constituted by braiding linear members or by covering the outer periphery of the stent with a film-like member.

Moreover, in the present embodiment, the forming of the connection member 34 in the rectangular shape has been described, but the other shapes such as elliptic and circular shapes may also be used as long as the doctor β easily grasps the member and the inner cylinder 24 is connected to the outermost cylinder 28 so as to be relatively immobile.

Figure 8A:
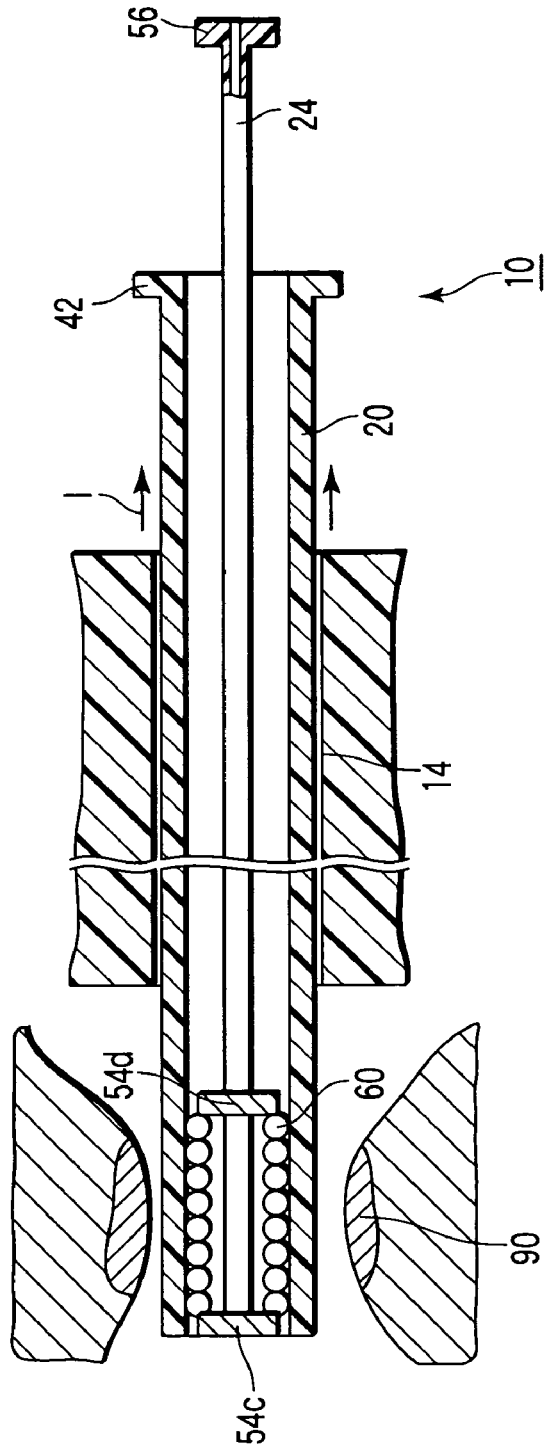
FIG. 8A is a schematic sectional view of the stent delivery system in a state in which the stent is attached to the stent delivery system according to a second embodiment.

Next, a second embodiment will be described with reference to FIG. 8 or 9B. The stent delivery system 10 of the present embodiment is a modification of the stent delivery system 10 described in the first embodiment, the same members as those described in the first embodiment are denoted with the same reference numerals, and the detailed description is omitted.

The stent delivery system 10 of the present embodiment includes the outer cylinder 20, the inner cylinder 24, a holder 120 attached to an operating section of the endoscope 80, and a fixing tool 125 disposed between the inner cylinder 24 and the holder 120.

Figure 8B:
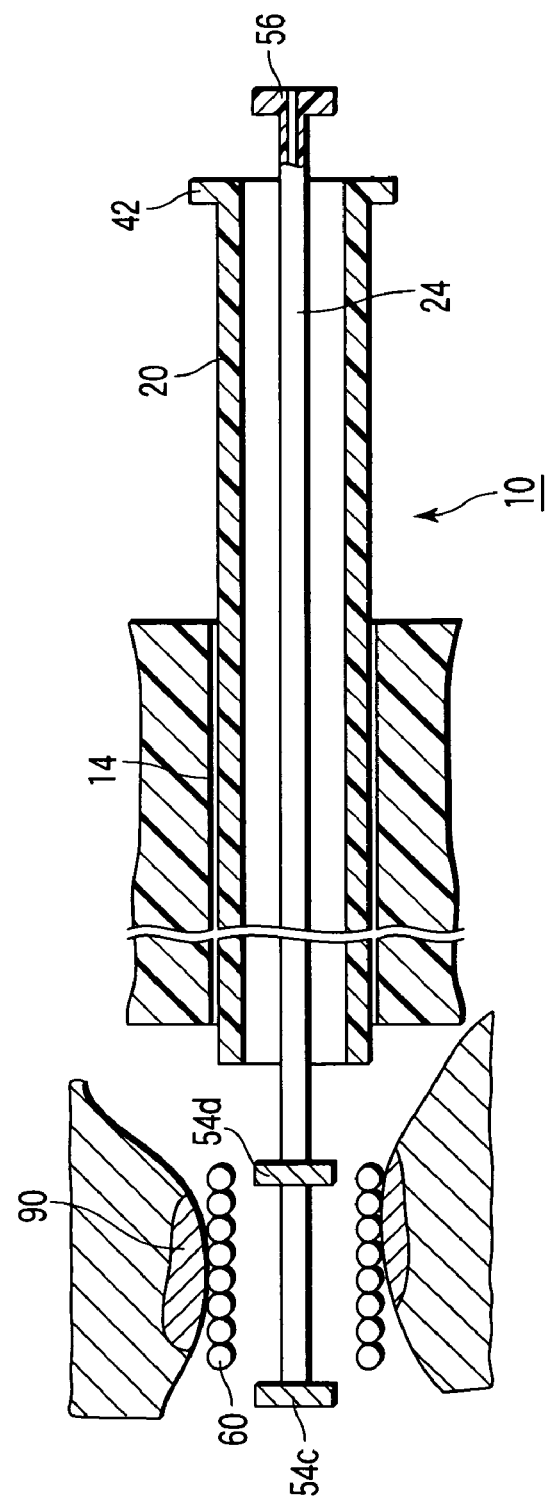
FIG. 8B is a schematic partial sectional view of the stent delivery system showing a state in which the stent of the stent delivery system according to the second embodiment is released from the regulated state.
Figures 9A, 9B:
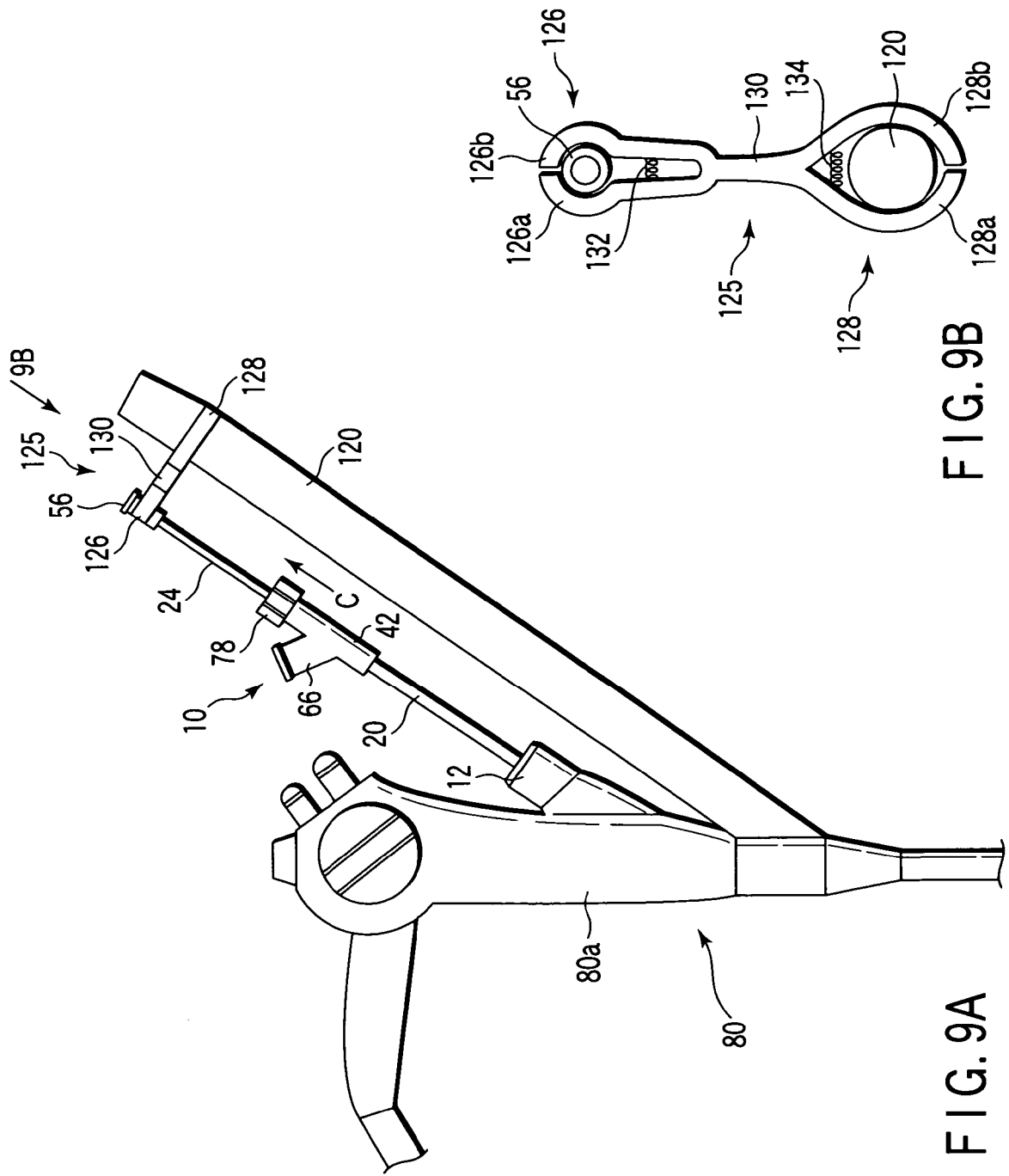
FIG. 9A is a schematic diagram showing a state in which the stent delivery system of the first embodiment is attached to the channel of the endoscope.
FIG. 9B is a schematic diagram seen from an arrow 9B direction in FIG. 9A.

As shown in FIG. 8, a main body of the stent delivery system 10 includes the outer cylinder 20 which contacts the inner wall of the forceps channel 14 of the endoscope 80, and the inner cylinder 24 inserted in the outer cylinder 20 so as to be capable of advancing/retreating. The stent delivery system 10 is different from that described in the first embodiment in that the outermost cylinder 28 is not disposed, and the tip-end chip 52 does not have to be disposed on the tip end of the inner cylinder 24. In this embodiment, X-ray chips 54c, 54d are bonded and fixed on the tip end of the inner cylinder 24 and in a position distant rearwards from the tip end by a predetermined distance. These X-ray chips 54c, 54d are formed in flange (annular) shapes outwards in the diametric direction of the inner cylinder 24. The self-expansion type stent 60 with the reduced diameter is disposed on the outer peripheral surface of the inner cylinder 24 between these tip-end chips 54c, 54d. The port 56 is connected to the base end of the inner cylinder 24. The guide wire can be inserted through the inner cylinder 24. Here, it is described that both the tip-end chips 54c, 54d are formed in the flange shapes, but the tip-end chip 54c does not have to be disposed in the flange shape. Even when the tip-end chip 54c does not have the flange shape, the stent 60 does not drop off the inner cylinder 24 during the relative movement of the outer cylinder 20 with respect to the inner cylinder 24 only on the hand side. Needless to say, it is preferable to dispose both the tip-end chips 54c, 54d in the flange shapes. When the outer cylinder 20 is advanced/retreated with respect to the inner cylinder 24, and when the outer cylinder 20 is disposed on the outer periphery of the stent 60, the stent 60 is prevented from moving (dropping from the inner cylinder 24).

For example, the substantially columnar holder 120 is extended from an operating section 80a of the endoscope 80. The holder 120 preferably straight extends substantially along the axial direction of the opening 12a of the forceps cap 12 disposed on the forceps channel 14.

The fixing tool 125 substantially capable of fixing the position of the port 56 with respect to the holder 120 is disposed between the holder 120 and the port 56 of the base end of the inner cylinder 24.

The fixing tool 125 includes a first grasp portion 126 which grasps the port 56 of the base end of the inner cylinder 24, a second-grasp portion 128 which grasps the holder 120, and a connection portion 130 which connects the first grasp portion 126 to the second grasp portion 128. The first and second grasp portions 126, 128 include pairs of arms 126a, 126b, 128a, 128b having elasticity, respectively. Each of springs 132, 134 is disposed between the pair of arms 126a and 126b, and 128a and 128b.

Therefore, the arms 126a, 126b of the first grasp portion 126 grasp the port 56 of the base end of the inner cylinder 24 by an urging force of the spring 132, and can then be fixed by a frictional force. The arms 128a, 128b of the second grasp portion 128 grasp the holder 120 by the urging force of the spring 134, and can then be fixed by the frictional force. These arms 126a, 126b, 128a, 128b are formed, for example, by an elastically deformable resin material, super-elastic material, or metal material.

Therefore, the fixing tool 125 is capable of fixing the inner cylinder 24 with respect to the holder 120. Therefore, the inner cylinder 24 is relatively fixed to the endoscope.

The holder 120 extended from the operating section 80a and the inner cylinder 24 extended outwards from the forceps cap 12 preferably hold a substantially parallel state. When this state is held, the relative position (distance) between the inner cylinder 24 and the holder 120 of the endoscope 80 can be brought into the fixed state (immobile state).

Next, the function of the stent delivery system 10 according to the present embodiment will be described. Description of the part similar to that of the function described in the first embodiment is omitted. The operation described below can be carried out by one doctor.

The tip end of the main body of the stent delivery system 10 is introduced into the bile duct via the guide wire, and the outer cylinder 20 is advanced/retreated/operated with respect to the forceps channel 14 and forceps cap 12 to position the tip end of the main body of the stent delivery system 10 in a target portion. The outer cylinder 20 is substantially fixed to the forceps channel 14 and forceps cap 12 by the friction between the outer wall of the outer cylinder 20, and the forceps channel 14 and forceps cap 12. Therefore, the outer cylinder 20 is positioned with respect to the target portion.

The arms 128a, 128b of the second grasp portion 128 are used to grasp and fix the fixing tool 125 in an appropriate position of the holder 120 attached to the operating section 80a of the endoscope 80. At this time, the fixing tool is prevented from dropping off the holder 120 by the urging force of the spring 134 between the arms 128a, 128b. The stent delivery system 10 is disposed substantially in parallel with the holder 120, and the port 56 and fixing tool 125 are grasped and fixed by the arms 126a, 126b of the first grasp portion 126. At this time, the fixing tool is prevented from dropping off the port 56 by the urging force of the spring 132 between the arms 126a, 126b.

The position of the fixing tool 125 on the holder 120 is adjusted so that an axis of the connection portion 130 of the fixing tool 125 is substantially vertical to that of the holder 120. Then, as shown in FIG. 9A, the relative position (distance) between the inner cylinder 24 and the holder 120 of the endoscope 80 is brought into the fixed state (immobile state). That is, the relative position between the inner cylinder 24 and the endoscope 80 is brought substantially into the fixed state.

When the stent 60 is indwelled, the rotary ring 78 of the connector 42 is rotated in a loosening direction, and the fixed state between the inner cylinder 24 and the outer cylinder 20 is released. The doctor holds the endoscope 80 with one hand, while drawing the connector 42 of the base end of the outer cylinder 20 back to the base end of the inner cylinder 24 with the other hand (direction of arrow C in FIG. 9A). That is, the outer cylinder 20 is pulled with respect to the inner cylinder 24 on the hand side (arrow I direction in FIG. 8A) against the frictional force of the forceps channel 14 and forceps cap 12 in the tip end of the main body of the stent delivery system 10.

At this time, the X-ray chip 54d prevents the stent 60 from moving in an arrow C direction together with the outer cylinder 20. Therefore, the stent 60 loses the regulation in the reduced diameter state by the outer cylinder 20 and expands from the tip-end side. When the connector 42 is further pulled in on the hand side, the outer cylinder 20 further moves rearwards with respect to the inner cylinder 24. Therefore, the stent 60 is exposed with respect to the body cavity, and the stent 60 expands toward the rear end and is released.

When the stent 60 is released, the fixing tool 125 is detached from the port 56, the stent delivery system 10 is pulled out of the forceps cap 12, and the indwelling of the stent 60 is completed.

As described above, the stent delivery system 10 of the present embodiment obtains the following effect.

The holder 120 of the endoscope 80 is relatively fixed to the inner cylinder 24 of the stent delivery system 10 via the fixing tool 125. Therefore, when the doctor operating the endoscope 80 simply advances/retreats/operates the connector 42 with respect to the inner cylinder 24 in the fixed state, the positional deviation of the inner cylinder 24 in which the stent 60 is charged is prevented, and the stent 60 can be indwelled in the desired position.

Therefore, the doctor operating the endoscope 80 can release the stent 60 alone without noticing the deviation of the position where the stent 60 is indwelled. Therefore, two doctors do not have to adjust the timings in performing the operation at the same time, the troublesome operation can be eliminated, and the operability of the stent delivery system 10 can be enhanced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A stent delivery system comprising:
a first cylindrical member configured to be inserted into a forceps channel of an endoscope, the first cylindrical member including a through hole having a central axis;
a second cylindrical member inserted into the through hole of the first cylindrical member and capable of advancing/retreating with respect to the first cylindrical member, the second cylindrical member including a holding mechanism for holding a relative position of the second cylindrical member with respect to the forceps channel of the endoscope; and
a stent which is attached between the first and second cylindrical members in a state where a diameter of the stent is reduced by the first cylindrical member and which expands when the first cylindrical member is removed;
wherein the holding mechanism includes a holder configured to be attached to and disposed on the endoscope and a fixing tool which connects the holder to the second cylindrical member in a detachably fixed state; and
the fixing tool includes:
an arm which grasps the holder; and
an arm which grasps the second cylindrical member.

2. A stent delivery system according to claim 1, wherein the second cylindrical member includes at least one X-ray chip recognized at the time of irradiation with an X-ray and disposed in a position where the stent is charged.

3. A stent delivery system according to claim 2, wherein the X-ray chip having a projection extending radially from an outer surface of the second cylindrical member.

4. A stent delivery system according to claim 3, wherein the holding mechanism includes:
a third cylindrical member directly slidable on the first cylindrical member outside the first cylindrical member and configured to be fixed to the forceps channel of the endoscope by friction; and
a connection member which connects the third cylindrical member to the second cylindrical member.

5. A stent delivery system according to claim 3, wherein the holding mechanism includes:
a third cylindrical member directly slidable on the first cylindrical member outside the first cylindrical member and configured to be fixed to a forceps cap disposed on a base end of the forceps channel of the endoscope by friction; and
a connection member which connects the third cylindrical member to the second cylindrical member.

6. A stent delivery system according to claim 3, wherein the holding mechanism includes:
a holder configured to be attached to and disposed on the endoscope; and
a fixing tool which connects the holder to the second cylindrical member in a detachably fixed state.

7. A stent delivery system according to claim 3, wherein at least the outer peripheral surface of the tip end of the first cylindrical member is coated with a hydrophilic lubrication.

8. A stent delivery system according to claim 3, wherein the second cylindrical member includes a tip-end chip coated with a hydrophilic lubrication on the tip end.

9. A stent delivery system according to claim 2, wherein static and dynamic frictions between the stent and the outer peripheral surface of the second cylindrical member are larger than the dynamic friction between the stent and the inner peripheral surface of the first cylindrical member.

10. A stent delivery system according to claim 9, wherein the holding mechanism includes:
a third cylindrical member directly slidable on the first cylindrical member outside the first cylindrical member and configured to be fixed to the forceps channel of the endoscope by friction; and
a connection member which connects the third cylindrical member to the second cylindrical member.

11. A stent delivery system according to claim 9, wherein the holding mechanism includes:
a third cylindrical member directly slidable on the first cylindrical member outside the first cylindrical member and configured to be fixed to a forceps cap disposed on a base end of the forceps channel of the endoscope by friction; and
a connection member which connects the third cylindrical member to the second cylindrical member.

12. A stent delivery system according to claim 9, wherein the holding mechanism includes:
a holder configured to be attached to and disposed on the endoscope; and
a fixing tool which connects the holder to the second cylindrical member in a detachably fixed state.

13. A stent delivery system according to claim 9, wherein at least the outer peripheral surface of the tip end of the first cylindrical member is coated with a hydrophilic lubrication.

14. A stent delivery system according to claim 9, wherein the second cylindrical member includes a tip-end chip coated with a hydrophilic lubrication on the tip end.

15. A stent delivery system according to claim 2, wherein the holding mechanism includes:
a third cylindrical member directly slidable on the first cylindrical member outside the first cylindrical member and configured to be fixed to the forceps channel of the endoscope by friction; and a connection member which connects the third cylindrical member to the second cylindrical member.

16. A stent delivery system according to claim 2, wherein the holding mechanism includes:
   a third cylindrical member directly slidable on the first cylindrical member outside the first cylindrical member and configured to be fixed to a forceps cap disposed on a base end of the forceps channel of the endoscope by friction; and
   a connection member which connects the third cylindrical member to the second cylindrical member.

17. A stent delivery system according to claim 2, wherein at least the outer peripheral surface of the tip end of the first cylindrical member is coated with a hydrophilic lubrication.

18. A stent delivery system according to claim 2, wherein the second cylindrical member includes a tip-end chip coated with a hydrophilic lubrication on the tip end.

19. A stent delivery system according to claim 1, wherein at least the outer peripheral surface of the tip end of the first cylindrical member is coated with a hydrophilic lubrication.

20. A stent delivery system according to claim 1, wherein the second cylindrical member includes a tip-end chip coated with a hydrophilic lubrication on the tip end.

21. An indwelling method for a stent using a stent delivery system comprising:
   a first cylindrical member configured to be inserted into a forceps channel of an endoscope, the first cylindrical member including a through hole having a central axis;
   a second cylindrical member inserted into the through hole of the first cylindrical member and capable of advancing/retreating with respect to the first cylindrical member, the second cylindrical member including a holding mechanism for holding a relative position of the second cylindrical member with respect to the forceps channel of the endoscope; and
   a stent which is attached between the first and second cylindrical members in a state where a diameter of the stent is reduced by the first cylindrical member and which expands when the first cylindrical member is removed;
   the method comprising the steps of:
   introducing the first cylindrical member and the second cylindrical member inserted inside the first cylindrical member to a target portion through the forceps channel of the endoscope while regulating expansion of the stent, which is a self-expansion type stent, charged over the second cylindrical member by the first cylindrical member;
   holding a relative position between the holding mechanism, which is attached to and disposed on the endoscope, and the second cylindrical member to regulate the movement of the second cylindrical member;
   pulling the first cylindrical member relative to the second cylindrical member, and expanding the stent to indwell the stent in the target portion; and
   releasing the regulation of the second cylindrical member to pull the second cylindrical member together with the first cylindrical member from the forceps channel of the endoscope.

* * * * *